United States Patent [19]

Dillon

[11] Patent Number: 5,084,281
[45] Date of Patent: Jan. 28, 1992

[54] METHOD AND SOLUTION FOR TREATING TISSUE WOUNDS

[76] Inventor: Richard S. Dillon, 150 Mill Creek Rd., Ardmore, Pa. 19003

[21] Appl. No.: 530,454

[22] Filed: May 29, 1990

Related U.S. Application Data

[63] Continuation of Ser. No. 310,740, Feb. 14, 1989, abandoned.

[51] Int. Cl.$^5$ .................... A61K 33/14; A61K 31/27; A61K 31/22; A61K 31/14
[52] U.S. Cl. ................... 424/677; 424/678; 424/679; 514/478; 514/546; 514/642
[58] Field of Search .............. 514/546, 478, 642; 424/677, 678, 679

[56] References Cited

U.S. PATENT DOCUMENTS

| 4,581,226 | 4/1986 | Dillon | 514/179 |
| 4,590,925 | 5/1986 | Dillon | 514/179 |

OTHER PUBLICATIONS

Goodman and Gillman, Sixth Edition, pp. 91-99 (1980).

Primary Examiner—Frederick E. Waddell
Assistant Examiner—Zolireh A. Fay
Attorney, Agent, or Firm—Dann, Dorfman, Herrell and Skillman

[57] ABSTRACT

A method and solution are disclosed for treatment of tissue wounds, particularly ulcerous lesions. The solution comprises a solution of seawater or a sea salt solution to which is added a cholinergic agent to stimulate local vasodilation and neurologic function.

15 Claims, No Drawings

METHOD AND SOLUTION FOR TREATING TISSUE WOUNDS

This application is a continuation of U.S. application Ser. No. 07/310,740, now abandoned, filed 2-14-89.

FIELD OF THE INVENTION

The present invention relates to treatment of tissue wounds, particularly ulcerous lesions occurring in body areas characterized by poor blood circulation in the tissue or by impaired neurologic function. The wound is treated by application of a salt and mineral solution having the characteristics of seawater to promote healing of the wound. The invention is particularly useful in the treatment of persistent lesions occurring on the extremities of a diabetic patient.

BACKGROUND OF THE INVENTION

The diabetic condition affects millions of people in the United States. Among the afflicted population, a significant percentage of persons develops problems associated with the lower extremities, namely, the foot and lower leg. In the diabetic, the foot represents an area which is repeatedly subjected to minor trauma which may be far more serious than in a healthy individual. Injury to the diabetic foot can result in ulceration which appears superficial, yet is capable of persistence and can lead ultimately to extensive tissue damage, gangrene of the feet or toes, systemic infection, and possibly may necessitate amputation of the compromised limb.

The long-term diabetic is unusually susceptible to a number of pathologic conditions, including macrovascular and microvascular disease. Arterial disease, including vascular occlusion of the lower extremities, is particularly common among the adult diabetic population.

In addition to arterial disorders, the diabetic is subject to peripheral neuropathy, which usually first manifests itself in the lower extremities. The neuropathic condition can exist either in association with, or independently of, vascular insufficiency. For example, a foot with seemingly good blood flow, as determined by inspection of foot color, foot temperature, or pedal pulse, may nonetheless exhibit neuropathy and loss or impairment of vasomotor nervous function. Although the underlying physiology and pathology of the condition is not well understood, it is possible that, in a neuropathic foot with apparently sufficient circulation, blood is nonetheless unable to sufficiently permeate the capillary beds and microvasculature to properly supply adjoining tissue.

The sensory impairment accompanying neuropathy in the diabetic makes the diabetic unusually prone to serious injury. Diabetic feet may be traumatized or subjected to infection in the same ways as normal feet; however, in the case of the neuropathic foot, the injury may not be properly sensed by the patient. For example, a diabetic with an ulcerous lesion or foot callus will not always tend to shift weight off of the damaged area of the foot, thereby greatly exacerbating the extent of tissue damage before the injury is detected.

Diabetic foot ulcers are further characterized by their persistent nature, which may arise primarily due to the arterial insufficiency and neuropathy of the local tissue and the entire limb. It is known that increasing circulation in the affected limb, and hence the area of the wound, will tend to promote healing. An apparatus for promoting blood circulation to a patient's extremity is described in U.S. Pat. No. 4,590,925, issued on May 27, 1986. The ischemic foot is benefitted by the resulting increase in peripheral circulation, which facilitates delivery of normal blood constituents, as well as systemically administered drugs or antibiotics, to the site of the ulcer or wound.

A different approach to restoring lost blood factors and cells to a foot ulcer is referred to as "clot therapy". In this procedure, which has met with some success, amounts of a patient's blood are applied directly to the ulcer bed to promote clotting and wound closure. Alternatively, a solution is prepared from platelets isolated from the patient's blood and the solution is applied directly to the ulcer bed. An antibiotic may be added to the solution or to the blood sample to control infection. The disadvantages associated with clot therapy are the requirement for a blood sample from the patient and the inconvenience attendant to applying the solution, which may involve immobilizing the patient and elevating the patient's limb, for the period that the blood or solution is applied and allowed to dry.

In U.S. Pat. No. 4,581,226, issued on April 8, 1986, a method is described for treating sensitive tissue, including foot ulcers, with a solution of processed seawater. The minerals, salts and other nutrient components of the processed seawater are disclosed to enhance healing of an ulcerous foot wound when applied as a soak solution.

SUMMARY OF THE INVENTION

The present invention is directed towards a treatment method and solution for tissue wounds characterized by depressed local blood circulation or by neuropathy. In particular, the treatment of persistent ulcerous lesions on the lower extremities of diabetic patients is contemplated. A method of treatment and a treatment solution for such tissue wounds is disclosed.

The solution of the invention consists essentially of a sterile, aqueous solution having the properties and characteristics of seawater, to which is added a cholinergic agent. The cholinergic agent preferably comprises a cholinergic stimulant in the form of a direct-acting choline ester. The seawater-like solution may be prepared from natural, off-shore seawater which has been suitably filtered and sterilized. Alternatively, sea salts and minerals may be prepared as an aqueous solution in sterilized water to achieve a seawater-like solution that possesses the major attributes of seawater in terms of composition.

In accordance with the method of the invention, the aforesaid solution is applied directly to the wounded tissue as a wash or wound soak.

DETAILED DESCRIPTION OF THE INVENTION

In accordance with the invention, a treatment solution is provided, which solution consists predominantly of a seawater-like solution. The solution may be prepared from actual seawater, in the manner described in U.S. Pat. No. 4,581,226, the entire disclosure of which is incorporated by reference herein as if set forth in its entirety. Summarizing briefly what is set forth fully in U.S. Pat. No. 4,581,226, seawater, preferably obtained at a site where there is little risk of contamination, is subjected to filtering and sterilization. The seawater is preferably diluted with tap water or distilled water to an osmolality compatible with human tissue. It is possible, and within the contemplated scope of the invention, to produce a seawater-like solution having the characteristics, qualities, and attributes, in terms of composition, of natural seawater. For example, sea salts obtained from distilled seawater are commercially available, and comprise the more common elements of seawater, such as calcium, magnesium, and potassium salts, as well as the numerous trace elements indigenous to seawater. Sea salts can be dissolved in an appropriate quantity of sterile water to achieve a solution having a salt and mineral content functionally comparable to natural seawater, and which, upon proper dilution, is compatible in osmolality with human tissue.

In a situation where seawater or sea salt is suspected to be contaminated, the predominant salts and minerals contained in seawater may be added to distilled water to provide an artificial sea salt solution which resembles seawater in its composition.

One important class of direct-acting cholinergic stimulants comprises the choline esters. Exemplary of the choline esters suitable for use in the treatment solution of the invention are bethanechol, methacholine, and carbachol.

Bethanechol is a carbamic acid ester of $\beta$-methylcholine, and the chloride salt of bethanechol (bethanechol chloride) is commercially available under the registered trademark "URECHOLINE" ® from Merck & Co., Inc. Bethanechol is a direct-acting cholinergic stimulant, e.g, it binds directly to and activates cholinergic receptors. In the body, it is capable of mimicking the effects of acetylcholine, its naturally-occurring analog. During stimulation of the parasympathetic nervous system, acetylcholine is released at postganglionic parasympathetic nerve endings. Acetylcholine is short-lived within the synapses, however, due to rapid inactivation by the enzyme acetylcholinesterase, which catalyzes the hydrolysis of acetylcholine to choline and acetic acid. Bethanechol, which is a synthetic analog of acetylcholine and mimics the effect of acetylcholine on cholinergic receptors, is resistant to hydrolysis by acetylcholinesterase. Accordingly, bethanechol achieves a longer-lasting stimulation of the parasympathetic nerve endings than its natural counterpart, acetylcholine. Alternatively, the solution may be prepared incorporating methacholine (acetyl-$\beta$-methylcholine) or carbachol (carbamoylcholine). Both methacholine and carbachol, like bethanechol, are resistant to the action of acetylcholinesterase. In the broadest sense of the invention, the cholinergic agent may consist of any one or more of the known parasympathomimetic agents, including both direct-acting and indirect acting cholinergic stimulants. Exemplary of such agents are the above-noted choline esters, the cholinergic alkaloids and their synthetic analogs, and the cholinesterase inhibitors. These compounds generally can stimulate, directly or indirectly, the desired response in tissue, and choice of the agent and its concentration in the solution may be ascertained by routine experimentation.

To prepare the treatment solution of the invention in its preferred form, the choline ester is added, preferably in the form of the chloride salt, to the seawater solution and dissolved therein. An amount of the chloride salt is added to render the resulting treatment solution effective in restoring local peripheral circulation. Circulation is improved by virtue of the vasodilator activity of the choline ester. Restoration of circulation to the damaged tissue area may also depend on restoration of nervous function in the infected local area by the action of the choline ester, which can help to restore the interrupted blood flow from the capillaries to the damaged tissue by improving impaired vasomotor activity.

By virtue of the increased blood flow to the site of tissue damage resulting from vasodilation and neurologic stimulation, the patient is able to supply blood to the tissue more effectively. Accordingly, the tissue is supplied with the platelets, blood factors, blood serum components, and immune effector cells which mediate tissue recovery and create a local microenvironment conducive to healing of the wound.

Local vasodilation and nervous stimulation of a wound area may be achieved to a satisfactory extent when the treatment solution is prepared by addition of approximately 2.5–100 milligrams of chloride salt to one liter of sterile, aqueous solution. The preferred solutions comprise about 2.5–50 milligrams of bethanechol chloride in one liter of solution, or about 25 to 100 milligrams methacholine in one liter of solution.

Bacterial infection of foot ulcers is quite common. Both gram-positive and gram-negative aerobic bacteria are frequently isolated from foot ulcers, and anaerobic organisms (e.g., peptococcus) are not infrequently present in the wound. For this reason, an antibiotic may be added to the treatment solution or used in conjunction therewith. A suitable antibiotic which is commonly applied to inflamed or infected skin areas is neomycin. Of course, it is possible to use cultures from the wound to identify particular microorganisms infecting a wound and select an appropriate antibiotic accordingly.

The treatment solution of the invention may be applied as a rinse or a wound soak. In the simplest applications, the solution is dabbed onto the wound with cotton on gauze. A wet dressing or gauze impregnated with the treatment solution may be applied and permitted to dry before applying fresh, wet dressing.

In a further embodiment of the method of the invention, the solution may be applied to treat damaged tissue on a patient's extremity, particularly an ulcer of the foot or lower leg, in conjunction with physical therapy designed to increase blood circulation to the extremity. For example, such therapy may include use of systems which are designed to increase blood flow to the foot, such as the system disclosed in U.S. Pat. No. 4,590,925, issued on May 27, 1986, the disclosure of which is incorporated by reference as if set forth fully herein.

The following Examples, in the form of illustrative patient case histories, will illustrate the effectiveness of the method and treatment solution of the invention. Examples I and II are comparative with Examples III and IV. Examples I and II set forth patient case histories wherein treatment was attempted with prior art methods, including "clot therapy" or treatment with seawater solution prepared in accordance with U.S. Pat. No. 4,581,226. Examples III and IV illustrate practice of the subject invention and illustrate the improved results obtained.

EXAMPLE I

Patient FF, a male, age 63, had a complex history of diabetes, multiple myeloma, amyloidosis, nicotine addiction and generalized arteriosclerotic cardiovascular disease. He had previously suffered two myocardial infarctions and an amputation of his left leg for gangrene. He was referred in the summer of 1977 with multiple gangrenous ulcers of his remaining right leg. Therapy with the device disclosed in U.S. Pat. No.

4,590,925 ("boot therapy") was effective in raising the subcutaneous oxygen level of his big toe from 12% to 68% of normal over a period of two weeks. Plaques of black eschar sloughed off his ankle and from all five toes. A large three by two inch eschar sloughed off the dorsum of his foot but the underlying ulcer was slow to heal. He received boot therapy three times a week over the next several months, which reduced the ulcer to approximately the size of a dime, but the ulcer could not be fully healed. In early May, 1978 his blood was clotted over his ulcer. A firm scab was left in place and observed over three days. The first two days it appeared to be doing well. The third day, however, pus was noted around the clot, the surrounding skin was red (cellulitic) and a red streak extended up his leg. Staphylococcus, Pseudomonas and Serratia were all cultured from the pus. The clot was soaked off and, fortunately, his infection responded to therapy with Carbenicillin. He was then admitted for a skin graft of the ulcer. Unfortunately, on the second hospital day he slipped and broke his hip delaying his surgery. While he healed his hip, he was treated with wet-to-dry dressings with seawater solution and nearly healed his ulcer reducing it to perhaps a quarter inch diameter. He missed his treatments for a few weeks, only to finally return with foot pain due to a new infection and lost his remaining leg.

EXAMPLE II

Patient CM, a male, age 77, had a 34 year history of diabetes. Gangrene had taken his left leg seven years previously. On Apr. 5, 1979, he was found to have an approximately ⅜th inch ulcer over a first metatarsal bunion and a plantar ulcer under his 5th metatarsal head. Rest, local debridements, antibiotics and consultations with his podiatrist, orthopod and surgeons were nonproductive. He returned for "boot therapy" and debridements of his callus. The plantar ulcer slowly healed but the bunion ulcer persisted. A small amount of Neomycin powder was mixed with his blood and puddled in his ulcer. He continued with intermittent "boot therapy" and "clot therapy" over a few months time as an outpatient as his ulcer slowly healed. His ulcer did not get infected with his "clot therapy" but its benefit was hard to assess and appeared slow and ineffective.

EXAMPLE III

Patient CP, a 52 year old female diabetic previously treated with oral agents, was referred on Feb. 4, 1988 with a plantar ulcer under her right foot that had not healed for over four years while under the care of her podiatrist. Her ulcer had resisted soaks, rest and local debridements of surrounding callus. A strong dorsalis pedis pulse attested to the presence of adequate blood flow. A two-point discrimination of 12 cm pointed to the presence of significant neuropathy. On Feb. 16, 1988, her ulcer measured 1.4×1.0 cm. She was then treated over a month as an outpatient with "boot therapy", resulting in a loss of the swelling in her foot, some improvement in sensation, and a measured improvement in her two-point discrimination to 6 cm. No change was detected in the size of her ulcer. She was hospitalized on Mar. 16, 1988 to insure bedrest and control of her diabetes. Her ulcer measurements did not change the first ten days in her hospitalization in spite of antibiotics, wet-to-dry soaks with sea salt solution (as disclosed in U.S. Pat. No. 4,581,226) Vancomycin, bedrest, the institution of insulin therapy, and "clot therapy". In the performance of "clot therapy", a two ml syringe containing 4 mg gentamicin (0.1 ml) was used to obtain a 1.8–1.9 ml sample of her blood which was mixed with the gentamicin. The latter mixture was then puddled on her ulcer and allowed to clot. The clot was applied in the evening and allowed to remain overnight. From March 18 to March 28, five such clots were applied. While the base of the ulcer appeared more shallow following this treatment, the ulcer changed little and still measured 0.9 by 0.6 cm on March 31. On April 4th, 50 mg bethanechol chloride was added to a half gallon of the sea salt solution previously used, and 0.1% Neomycin was added, and the solution applied as a wet-to-dry dressing. The dressings were changed every two hours during the day with an obvious effect on the rate of healing. Even though her ulcer was not fully healed, and still measured 0.7 cm×0.4 cm on April 15th, she was discharged on April 16th to continue the soaks at home. Following such treatment, the ulcer appeared fully closed to visual inspection by April 28. On May 10th, callus forming over the area was shaved off revealing normal underlying tissue.

EXAMPLE IV

Patient VK, a male, was admitted at age 63 with type II diabetes, diabetic retinopathy, peripheral neuropathy, medial calcinosis of the arteries in his feet, splits in his heels, calluses on both soles, and a 2.5×1.8 cm ulcer under his left first metatarsal head. The ulcer had reportedly persisted in spite of multiple therapies by various physicians over a period of three years. In addition, the lower two-thirds of his left leg was reddened and swollen. He could not feel a stick pressed against his distal foot. Venous testing pointed to superficial phlebitis in the calf and arterial testing showed pseudohypertension at the ankle compatible with his medial calcinosis. He was initially treated with heparin, parenteral antibiotics, and a sea salt solution with 5% Betadine as a soak four times a day. "Boot therapy" was then begun, successfully reducing the swelling of his leg and increasing sensation in his foot. Treatment soaks using the solution of the invention (about 50 mg bethanechol chloride added to one half gallon sterile, diluted seawater) were begun when it became apparent his ulcer was not responding. Following treatment soaking with the solution of the invention, his ulcer appeared to respond and decreased over the next several days to 30% of its original size. He was discharged and given a quantity of solution to continue the soaking treatment. He was not available for close visual follow-up, but was reached on the telephone and claims to be responding well to the treatment.

While certain preferred embodiments of the invention have been illustrated and described in the foregoing examples and written description, the present invention is not limited thereto. Other modifications to the method and solution to the invention may be made by one skilled in the art within the scope of the following claims.

I claim:

1. A topically applied composition for treating persistent, neuropathic dermal ulcers said composition consisting essentially of:
   a) a sterile, aqueous solution of minerals and salts having the compositional characteristics of seawater; and
   b) an amount of a cholinergic agent effective to achieve enhanced local vasodilation and neurologic stimulation within said ulcer to promote healing thereof.

2. A composition as set forth in claim 1 wherein said cholinergic agent is selected from the group consisting of methacholine, bethanechol and carbachol.

3. A composition as set forth in claim 2 wherein said sterile, aqueous solution comprises a solution prepared by processing seawater to separate debris and small organisms therefrom.

4. A composition as set forth in claim 3 wherein said solution is diluted to be isotonically compatible with human serum.

5. A composition as set forth in claim 2 comprising the chloride salt of said cholinergic agent.

6. A composition as set forth in claim 5 wherein said chloride salt consists of bethanechol chloride.

7. A composition as set forth in claim 6 wherein said bethanechol chloride is present in an amount from about 2.5 to about 50 milligrams per liter of sterile, aqueous solution.

8. A composition as set forth in claim 5 wherein said solution further contains an antibiotic.

9. A method for treatment of a persistent, neuropathic dermal ulcer comprising applying to said wound a composition consisting essentially of a sterile, aqueous solution of minerals and salts having the compositional characteristics of seawater, and an amount of a cholinergic agent effective to achieve enhanced local vasodilation and neurologic stimulation within said ulcer to promote healing thereof.

10. A method as set forth in claim 9 wherein said composition is applied to an ulcer located on a human extremity.

11. A method as set forth in claim 9 wherein said composition is applied to a foot ulcer.

12. A method as set forth in claim 10 which comprises applying said composition in conjunction with physical therapy designed to increase circulation to said extremity.

13. A method as set forth in claim 9 wherein said ulcer is irrigated periodically with said composition.

14. A method as set forth in claim 9 wherein said composition is applied to said ulcer as a wet dressing.

15. A method for treating neuropathic foot ulcers, consisting of applying to said ulcer a composition consisting essentially of a sterile, aqueous solution of minerals and salts having the compositional characteristics of seawater, and an amount of a direct-acting cholinergic stimulant effective to achieve enhanced local vasodilation and neurologic stimulation within said ulcer to promote healing thereof.

* * * * *